(12) United States Patent
Unidad et al.

(10) Patent No.: US 11,249,941 B2
(45) Date of Patent: Feb. 15, 2022

(54) EXABYTE-SCALE DATA STORAGE USING SEQUENCE-CONTROLLED POLYMERS

(71) Applicant: PALO ALTO RESEARCH CENTER INCORPORATED, Palo Alto, CA (US)

(72) Inventors: Jerome Unidad, San Francisco, CA (US); David Mathew Johnson, San Francisco, CA (US); Elif Karatay, Mountain View, CA (US); Mahati Chintapalli, Mountain View, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 388 days.

(21) Appl. No.: 16/229,306

(22) Filed: Dec. 21, 2018

(65) Prior Publication Data

US 2020/0201812 A1 Jun. 25, 2020

(51) Int. Cl.
*G06F 16/11* (2019.01)
*G01N 21/64* (2006.01)
(Continued)

(52) U.S. Cl.
CPC ........... *G06F 16/116* (2019.01); *B41M 3/006* (2013.01); *G01N 21/64* (2013.01); *G01N 33/442* (2013.01)

(58) Field of Classification Search
CPC .... G06F 16/116; G01N 21/64; G01N 33/442; B41M 3/006
(Continued)

(56) References Cited

U.S. PATENT DOCUMENTS

| 7,252,938 B2 * | 8/2007 | Leproust | B01J 19/0046 |
| | | | 435/286.2 |
| 7,727,678 B2 * | 6/2010 | Stadler | G11B 7/253 |
| | | | 430/1 |

(Continued)

FOREIGN PATENT DOCUMENTS

WO WO-2017189914 A1 * 11/2017 ............. G06N 3/123

OTHER PUBLICATIONS

Mansuripur et al., "Information Storage and Retrieval using Macromolecules as Storage Media," in Optical Data Storage, OSA Technical Digest Series (Optical Society of America, 2003), paper TuC2, 2003, pp. 109-111. (Year: 2003).*
(Continued)

*Primary Examiner* — Phuong Thao Cao
(74) *Attorney, Agent, or Firm* — Miller Nash LLP

(57) ABSTRACT

A method of storing digital data in non-biological sequence-controlled polymers includes converting a digital data file into a monomer sequence, synthesizing polymer chains according to the monomer sequence, and encapsulating the polymer chains into microfluidic droplets and providing the microfluidic droplets with addresses. A polymer data storage system has a first converter to convert digital data to a polymer sequence, a polymer synthesizer to produce polymer chains according to a pre-determined monomer sequence, a fluidic encapsulation system to encapsulate the polymer chains in microfluidic droplets and to apply addressing materials to the microfluidic droplets, a storage for storing the microfluidic droplets, a droplet sorting system having at least an actuator to sort the droplets, a sequencer to derive the polymer sequence from the polymer chains contained in the droplets, and a second converter to convert the polymer sequence to digital data. A composition of matter wherein polymer chains comprising alternating segments of flexible linkers and one or more rigid monomer
(Continued)

blocks, and wherein the rigid blocks are defined in a meaningful manner to store in a sequence in the polymer chain that represents digital data.

19 Claims, 10 Drawing Sheets

(51) Int. Cl.
  *B41M 3/00* (2006.01)
  *G01N 33/44* (2006.01)
(58) Field of Classification Search
  USPC .......................................................... 707/822
  See application file for complete search history.

(56) References Cited

U.S. PATENT DOCUMENTS

| | | | |
|---|---|---|---|
| 9,834,642 B2 | 12/2017 | Lutz et al. | |
| 9,928,869 B2* | 3/2018 | Church | C12Q 1/68 |
| 10,370,246 B1* | 8/2019 | Milenkovic | G16B 50/00 |
| 10,839,948 B2* | 11/2020 | Bramlett | G16H 10/60 |
| 2001/0039014 A1* | 11/2001 | Bass | C12N 15/1031 |
| | | | 435/6.11 |
| 2003/0017261 A1* | 1/2003 | Han | G11B 7/25 |
| | | | 427/162 |
| 2004/0001371 A1 | 1/2004 | Mansuripur et al. | |
| 2006/0068318 A1* | 3/2006 | Meagley | G03F 7/0392 |
| | | | 430/270.1 |
| 2008/0076903 A1* | 3/2008 | Duerig | C08G 73/101 |
| | | | 528/310 |
| 2008/0205253 A1* | 8/2008 | DiPietro | C08G 65/46 |
| | | | 369/154 |
| 2010/0137163 A1* | 6/2010 | Link | B82Y 5/00 |
| | | | 506/16 |
| 2011/0177980 A1* | 7/2011 | Lin | B82Y 10/00 |
| | | | 506/37 |
| 2012/0252007 A1* | 10/2012 | Rabbani | C12Q 1/6876 |
| | | | 435/5 |
| 2013/0273068 A1* | 10/2013 | Rohlff | C07K 16/40 |
| | | | 424/158.1 |
| 2013/0344561 A1* | 12/2013 | Davidson | C12N 9/1241 |
| | | | 435/178 |
| 2014/0120604 A1* | 5/2014 | Aguanno | B01L 3/502715 |
| | | | 435/287.2 |
| 2015/0231254 A1* | 8/2015 | Sleiman | A61K 47/545 |
| | | | 424/489 |
| 2015/0298091 A1* | 10/2015 | Weitz | B01J 19/0046 |
| | | | 506/16 |
| 2015/0328616 A1* | 11/2015 | Gethers | B01J 19/0046 |
| | | | 506/16 |
| 2016/0004815 A1* | 1/2016 | Lerner | G16B 20/00 |
| | | | 702/19 |
| 2016/0222162 A1* | 8/2016 | Lutz | H04K 1/00 |
| 2016/0257785 A1* | 9/2016 | Grate | C08G 73/065 |
| 2016/0310926 A1* | 10/2016 | Sun | C12Q 1/6804 |
| 2017/0017436 A1* | 1/2017 | Church | G11B 7/241 |
| 2017/0114341 A1* | 4/2017 | Bradshaw | C07H 21/04 |
| 2017/0130258 A1* | 5/2017 | Sampas | C12Q 1/686 |
| 2017/0147746 A1* | 5/2017 | Healy | G16B 30/00 |
| 2017/0227440 A1* | 8/2017 | Smith | B01L 3/502784 |
| 2018/0104693 A1* | 4/2018 | Merten | G01N 15/1484 |
| 2018/0161447 A1* | 6/2018 | Watson | A61K 31/7105 |
| 2018/0189448 A1* | 7/2018 | Bramlett | G16H 10/60 |
| 2018/0253528 A1* | 9/2018 | Strauss | G16B 30/00 |
| 2018/0298154 A1* | 10/2018 | Lundorf | C09D 11/04 |
| 2018/0362969 A1* | 12/2018 | Banal | C12P 19/34 |
| 2019/0050495 A1* | 2/2019 | Su | G16B 50/50 |
| 2019/0062258 A1* | 2/2019 | Upton | C07C 51/412 |
| 2019/0136307 A1* | 5/2019 | Predki | C12P 19/34 |
| 2019/0139603 A1* | 5/2019 | Mosbach | B01J 20/268 |
| 2019/0291106 A1* | 9/2019 | Jans | B01L 3/502715 |
| 2019/0351673 A1* | 11/2019 | Roquet | G06N 3/123 |
| 2019/0362814 A1* | 11/2019 | Roquet | H03M 7/40 |
| 2019/0363739 A1* | 11/2019 | Erlich | G16C 20/10 |
| 2020/0193301 A1* | 6/2020 | Roquet | G16B 50/20 |
| 2020/0327421 A1* | 10/2020 | Bathe | G06N 3/123 |
| 2020/0361996 A1* | 11/2020 | Pochan | A61K 47/6903 |
| 2020/0407503 A1* | 12/2020 | Lutz | C09D 125/06 |
| 2020/0407697 A1* | 12/2020 | Shepherd | C12N 15/1037 |

OTHER PUBLICATIONS

Pon et al., "Linker phosphoramidite reagents for the attachment of the first nucleoside to underivatized solid-phase supports," Nucleic Acids Research, 2004, vol. 32, No. 2, pp. 623-621, DOI: 10.1093/nar/gkh222. (Year: 2004).*
Tusy et al., "Effect of flexible linker length in 3,4-ethylenedioxythiophene derivatives for solid state polymerization," RSC Advances, 2015, 5, pp. 16292-16301. (Year: 2015).*
Klein et al., "Design and characterization of structured protein linkers with differing flexibilities", Protein Engineering, Design & Selection, vol. 27, No. 10, pp. 325-330, 2014. (Year: 2014).*
Lutz, Jean-Francois, "Coding Macromolecules: Inputting Information in Polymers Using Monomer-based Alphabets", Macromolecules, 2015, 48, pp. 4759-4767. (Provided by Applicant) (Year: 2015).*
Lutz et al., "Sequence-Controlled Polymers", Science, Aug. 9, 2013, vol. 341, 1238149 (2013). (Year: 2013).*
Roy et al., "Design and synthesis of digitally encoded polymers that can be decoded and erased", Natural Communications 6, 7237 (2015), published May 26, 2015, 8 pages. (Year: 2015).*
Li et al., "Synthesis and Self-Assembly of Coil-Rod Double Hydrophilic Diblock Copolymer with Dually Responsive Asymmetric Centipede-Shaped Polymer Brush as the Rod Segment", Macromolecules, vol. 42, No. 8, 2009, pp. 2916-2924. (Year: 2009).*
"Belgian PhD Student decodes DNA and wins a Bitcoin," EMBL-EBI, https://www.ebi.ac.uk/about/news/press-releases/belgian-phd-student-decodes-dna-wins-bitcoin printed Apr. 11, 2019.
Erlich and Zielinski, "DNA Fountain enables a robust and efficient storage architecture," Science 355, 950-954, Mar. 3, 2017.
Goldman et al., "Toward practical high-capacity low-maintenance storage of digital information in synthesised DNA," Nature, 494(7435): 77-80, Feb. 7, 2013.
Kiesel, et al. "Spatially modulated fluorescence emission from moving particles," Applied Physics Letters 94: 041107 (2009).
Kwok et al., "Nanopore Fabrication by Controlled Dielectric Breakdown," Plos One, vol. 9, Issue 3, Mar. 2014, 5 pages.
Lutz, "Coding Macromolecules: Inputting Information in Polymers Using Monomer-Based Alphabets," Macromolecules 48, 4759-4767 (2015).
Church et al., "Next-Generation Digital Information Storage in DNA," Sciencexpress, http://www.sciencemag.org/content/early/recent / Aug. 16, 2012 / Page 1/ 10.1126/science.1226355.
Ouahabi et al., "Mass spectrometry sequencing of long digital polymers facilitated by programmed inter-byte fragmentation," Nature Communications 8:967, Oct. 17, 2017.
Rosenstein et al., "Integrated nanopore sensing platform with sub-microsecond temporal resolution," www.nature.com/naturemethods/ Published online Mar. 18, 2012.
Roy et al., "Design and synthesis of digitally encoded polymers that can be decoded and erased," Nature Communications 6:7237, May 26, 2015.
Where in the World is Storage—Byte Density Across the Globe, IDC Infographic, 2017, found at https://www.idc.com/downloads/where_is_storage_infographic_243338.pdf.

* cited by examiner

| | COMMON FLEXIBLE LINKER | INFORMATION-ENCODING RIGID MONOMERS/OLIGOMERS |
|---|---|---|
| 4 CHARACTER MONOMER ALPHABET | A~~~A | B-[rect]-B<br>B-(oval)-B<br>B-(diamond)-B<br>B-(circle)-B |
| 8 CHARACTER MONOMER ALAPHABET | A~~~A | B-[rect]-B, B-[square]-B<br>B-(oval)-B<br>B-(diamond)-B, B-(diamond)-B<br>B-(circle)-B<br>B-(bowtie)-B, B-(hexagon)-B |
| 4 CHARACTER MONOMER ALPHABET | A~~~C | B-[rect]-D<br>B-(oval)-D<br>B-(diamond)-D<br>B-(circle)-D |
| 8 CHARACTER MONOMER ALAPHABET | A~~~C | B-[rect]-D, B-[square]-D<br>B-(oval)-D<br>B-(diamond)-D, B-(diamond)-D<br>B-(circle)-D<br>B-(bowtie)-D, B-(hexagon)-D |

FIG. 2

EXABYTE-SCALE DATA STORAGE USING SEQUENCE-CONTROLLED POLYMERS

TECHNICAL FIELD

This disclosure relates to Exabyte-scale data storage, more particularly to storing digital data as a monomer sequence.

BACKGROUND

Data is one of the most important resources in today's information-driven society. There's an emerging need for archiving digital data in a form that allows retrieval over a long period of time. This demand for data storage technologies has been exponentially-growing as we generate more and more data through the ubiquity of sensing and computing modalities but the capacity of existing data storage methods has not been keeping up. For an example, the IDC estimate that entirety of the digital universe to be 16 Zettabytes (1 Zb=$10^{21}$ Bytes). For the data fraction that we choose to archive, the incumbent storage medium is magnetic tape due to its extended longevity of up to 30 years when kept in optimal environmental conditions, typically cold storage. The infrastructure and cost for magnetic tape storage is however very high and resource-intensive. Recently, Facebook constructed an Exabyte (1 Eb=$10^{18}$ Bytes) data center which has a capacity of 1 Eb spread over several acres of land and an energy footprint of about 200 MW. This places the 10-year total cost of ownership to be about 1 billion dollars.

As a solution to the non-tractable, resource-intensive mode for state-of-the-art data storage, people have started looking at alternative data storage media such as DNA. There had been earlier suggestions of using DNA to store data from decades past since DNA is a relatively stable biomolecule and can store biological information for centuries. The main bottleneck was, however, the synthesis of arbitrary DNA sequences to be mapped to digital data on-demand, so-called de novo synthesis, and the ability to sequence the DNA, spurred by advances in genomic tools and next-generation sequencing.

In fact, the modern era of DNA data storage started around 2012 from a paper published by George Church and co-workers of Harvard University, who made advances in de novo DNA synthesis and reported the storage and retrieval of several files, totaling about 643 kB in de novo synthesized DNA. Shortly thereafter, Nick Goldman and colleagues from the European Bioinfomatics Institute reported a similar effort and stored about 739 kB. In addition, Goldman launched the Davos bitcoin challenge and distributed multiple copies of their DNA encoded information to anyone would want to decode it, with the promise of a bitcoin for the first successful decoding. Since then, multiple other groups have demonstrated digital data storage in DNA in various capacities.

These include the advances by the Microsoft-University of Washington collaboration which in 2018 reported the largest encoded synthetic DNA pool to-date, corresponding to 200 MB with random access capability of up to 48 addressable mini-files out of their total of 3240 pools, which is the largest level of random access at present. In terms of encoding efficiency and the realization of the theoretical Shannon capacity of DNA, the most advanced coding scheme, binary sequence to DNA nucleotide sequence, is that of Erlich and Zielinski which enables an 86% realization of the Shannon capacity of DNA although their system does not provide random access capability.

While strides have been made to advance DNA data storage into its present level, most approaches rely on the current hardware layer that DNA data storage inherits from modern biotechnology. For example, on-demand de novo synthesis of DNA sequences for information writing and next-generation sequencing technologies for information reading. The workflow for these processes, particularly the writing part typically rely on off-site processes, such as Twist Bioscience for DNA synthesis. In contrast, sequencing is slowly moving from sequencing-by-synthesis approaches, as in Illumina MiSeq, to next-generation sequencing approaches—such as that by nanopores, such as Oxford Nanopore MinION, small devices that are easy to integrate in more self-contained workflow. As such, the main bottleneck for further scaling and future economic viability is the information writing step which is currently expensive and limited in the length of DNA oligonucleotides that can be synthesized (typically 150-200 nucleotides). There are still strides to be made in terms of information reading, for example to make the reads more accurate and faster but the cost of sequencing has been driven down largely by the genome project.

SUMMARY

According to aspects illustrated here, there is provided a method of storing digital data in non-biological sequence-controlled polymers that includes converting a digital data file into a monomer sequence, synthesizing polymer chains according to the monomer sequence, and encapsulating the polymer chains into microfluidic droplets and providing the microfluidic droplets with addresses.

According to aspects illustrated here, there is provided a polymer data storage system that has a first converter to convert digital data to a polymer sequence, a polymer synthesizer to produce polymer chains according to a predetermined monomer sequence, a fluidic encapsulation system to encapsulate the polymer chains in microfluidic droplets and to apply addressing materials to the microfluidic droplets, a storage for storing the microfluidic droplets, a droplet sorting system having at least an actuator to sort the droplets, a sequencer to derive the polymer sequence from the polymer chains contained in the droplets, and a second converter to convert the polymer sequence to digital data.

According to aspects illustrated here, there is provided a composition of matter wherein polymer chains comprising alternating segments of flexible linkers and one or more rigid monomer blocks, and wherein the rigid blocks are defined in a meaningful manner to store in a sequence in the polymer chain that represents digital data.

BRIEF DESCRIPTION OF THE DRAWINGS

FIG. 2 shows an embodiment of information encoding using monomers and oligomers.

DETAILED DESCRIPTION OF THE EMBODIMENTS

The embodiments detail a method for digital data storage using non-biological, sequence-controlled polymers for eventual use for Exabyte-scale archival data storage. In these embodiments, the digital data that takes the form of a string of binary characters, is and Os, are mapped into a monomer sequence based on a pre-defined encoding scheme consisting of distinguishable information encoding monomers. The system then synthesizes a small amount of polymer molecules with an exact sequence corresponding to the monomer sequence. The data is then stored in the form a physical molecule as a sequence of monomers.

The data can be retrieved by "sequencing" a molecule from the set, generally involving the use of a physical measurement to determine the monomer sequence built-in and then reversely decoded to reveal the digital data. The polymer chains can be stored as microfluidic droplets in the short-term, which are optically labelled with specific dye combinations to determine their address in terms of a bigger archive. Alternatively, the polymer chains can be dehydrated and turned into powder, frozen, coated with a polymer shell or stored in some other manner for long-term storage, and stored in specific compartments for physical addressing.

The motivations behind using non-biological, synthetic polymers, and sequence controlled polymers includes the availability of a larger alphabet for monomer selection that in turn enables larger bit encoding per monomer sequence than DNA, which is limited to 2-bit encoding per nucleotide. Other advantages include the ability to polymerize synthetic polymers to larger lengths and using more scalable methods, and the ability to design synthetic polymers for ease of sequencing using existing methods. This means that the monomer properties and polymer architectures can be tuned to particular ways of sequencing. For example, as will be discussed further, one embodiment uses a nanopore array for sequencing the polymers. These have limited applicability for DNA sequencing, but for suitably-designed polymers they can provide size tenability and can be fabricated in larger arrays. Synthetic polymers could also be designed to be more thermally and chemically stable than DNA, which imparts a longer shelf life for their use as data storage medium.

Figure 1:
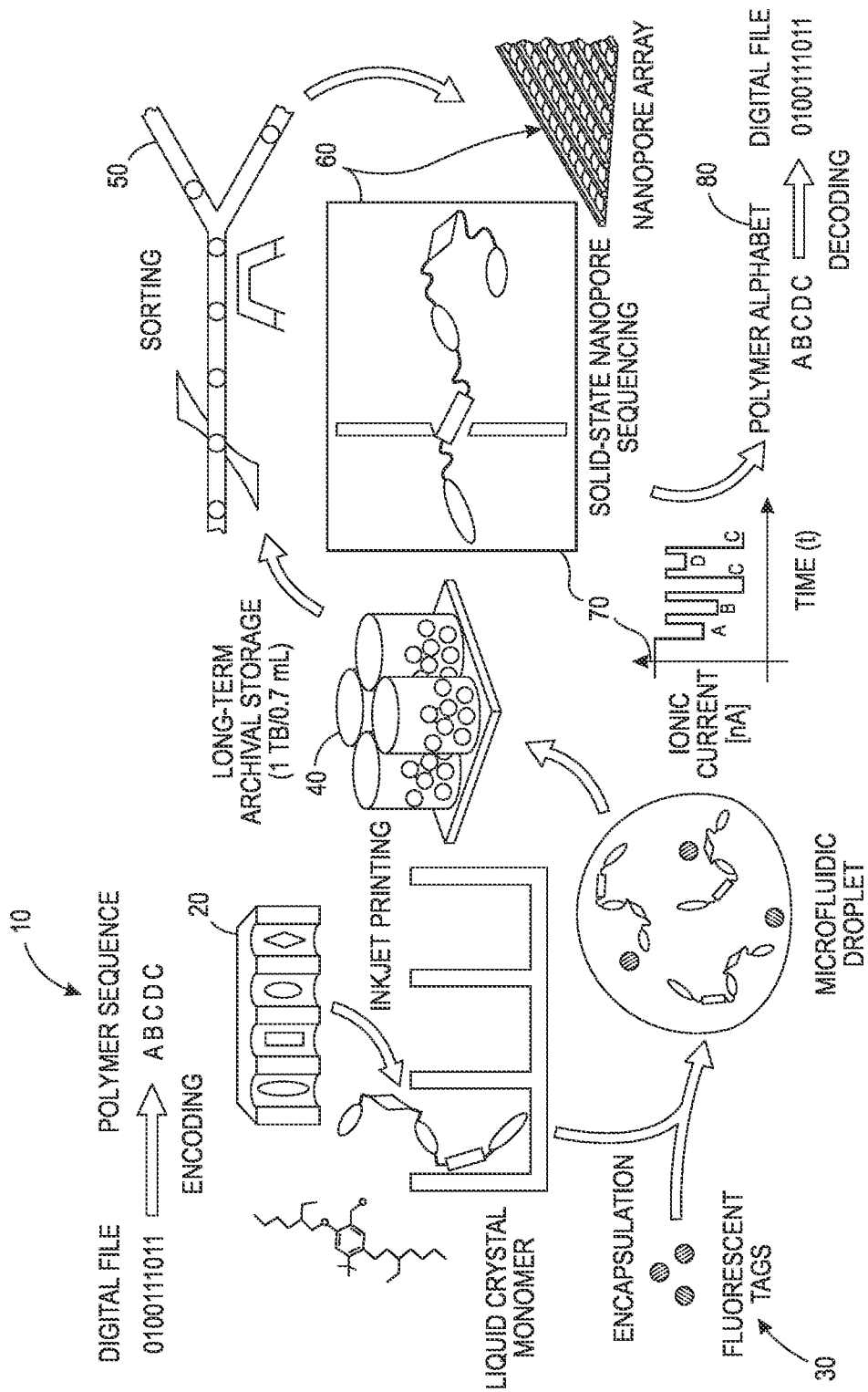
FIG. 1 shows an embodiment of an Exabyte encoding, storage and retrieval system.

The embodiments here include a method and a system for large scale data storage using polymers. The system may be referred to as SCRIPT—Scalable, Robust Information Storage using Polymer Technology. FIG. 1 shows one embodiment of the SCRIPT system and method. In general, the process has two parts, data storage and data retrieval.

As shown in FIG. 1, the data storage process begins at 10 with the conversion of the digital data into a polymer 'sequence' in which each character in the sequence is a combination of monomers in a particular sequence. This process may also be referred to data conversion or data translation. The process of data conversion is not restricted to the conversion of a binary string into a polymer sequence as data in other encoding schemes (hexadecimal, etc.) could also be translated to a suitable polymer sequence. In the case illustrated, the input binary file is mapped to a polymer sequence using an alphabet of 4 information-encoding monomers or characters.

Once the monomer sequences are determined, a synthesizer synthesizes the polymers to be made up of these particular monomer sequences at 20. As will be discussed in more detail, one method of synthesizing the polymers involves inkjet printing. Once the polymer chains are formed, they are encapsulated in a microfluidic droplet and provided an address at 30. In one embodiment, the address is an optical address achieved by a particular emission at a certain optical wavelength and the intensity of the emission. For example, the optical address would not only comprise of the wavelength of the emission but it would include variations of intensity of the emission and combinations of intensity-encoded emissions at different wavelengths. The microfluidic droplet collocates the dyes to the particular polymer chains contained within. For error correction, as will be discussed in more detail later, the microfluidic droplet may contain thousands or even millions of copies of the particular polymer chain.

Once the droplets are addressed, they can be stored. For shorter term storage, they could just remain in a container, such as a beaker. Over time, the polymer chains may start to migrate out of the droplets, or the droplets may start to aggregate, causing droplets with different addresses and information to mix together. Long term storage may involve drying, freezing the droplets or encapsulation with a polymer shell to stop the mixing and chemical degradation of the data.

Once the droplets are stored, in order to access the data, they must be retrieved, sorted and accessed to determine the monomer sequence, and then converted back to digital data. Sorting the droplets at 50 depends upon the means of addressing. In the embodiment where the droplets were optically addressed, a light source or sources is used to identify a particular color and intensity of droplets and then an actuator applies a specific form of energy, discussed later, to sort the droplets. As the droplets are being sorted, they are deposited in a readout array at 60. In one embodiment, the array comprises a solid-state, nanopore array where each droplet gets deposited into a holding chamber above each array. In other embodiments, the droplets are directed in some way to other sequencing approaches such as microfluidic-based mass spectrometers, known in the art and used for other applications such as proteomics and chemical analysis.

At 70, polymer chains from the holding chambers go through the nanopore and are characterized to determine the characters of the polymer alphabet contained in the chain. The result of this process is some physical measurement of the polymer sequence. For the illustrated embodiment at 70, this physical measurement is a readout of the ionic current as a function of time that is mapped out into a polymer sequence. At 80 the characters are then converted to digital data. In the following figures, portions of this process will be addressed in more detail, referring back to FIG. 1.

The discussion turns first to how the digital file is to be converted to a sequence of monomers that will form the polymer. One example is shown in FIG. 1, where there are four characters in the 'polymer' alphabet, A, B, C and D. Each 2-bit binary term equates to one of the characters, 01 equals A, 00 equals B, 11 equals C, and 10 equals D. The string 0100111011 becomes A-B-C-D-C. This then guides the synthesis module that will lead to the formation of the polymer chains. In other embodiments, more sophisticated mapping schemes could be used in this conversion, e.g.

mapping longer strings of binary digits to a pre-set basis sequence of several characters or monomers called codons (as occurring naturally in the translation of RNA to amino acid sequences). Other variants may use methods known in communication systems (Block codes, Fountain codes, etc.) to make the data storage channel more robust and less error-prone.

In FIG. 2, the top two lines address either a 4-character or an 8-character alphabet both using a common linker represented as A-A, which means that each end of the linker has the same functional group. Possibilities for linkers include polystyrene sulfonate, but other charged polymers such as polyanions and polycations, including polyacrylic acid, polylactic acid, etc. could also be used. These flexible linkers are ideally defined by a small persistence length (≤2 nm). Some of these flexible linkers can be polymerized using living anionic polymerization, and other forms of controlled polymerization, to obtain near uniform chain length. The first linker used to connect the initial monomer in the sequence to the microbead may be different than the linkers, referred to here as the second linkers that connect monomer to monomer.

Each shape on the right side represents a different monomer, 4 in the top line and 8 in the second. The rigid polymers may include any polymer that has a rod-like structure, polymers that have a large persistence length (≥2 nm) and/or polymer units that are bulky and have a large packing length (≥6 Angstroms). These may include mesogenic or liquid crystalline polymers. As used here the term 'rigid' includes those types of polymers. Examples include, without limitation: amylose; polyacetylene; poly(p-benzamide); poly((bensobishiazole-2,6-diyl)-4,4-phenylene); poly(2,5-benzophenone); poly(γ-benzyl-L-glutamate); poly-N-hexyl-isocyanate; poly-trifluoroacetyl-L-lysine; poly(2,5-bis[(4-methoxyphenyl)oxycarbonyl]styrene); poly(2,5-bis[4-methylbutoxy)phenyl]styrene); poly-diethylhexyloxy-p-phenylenevinylene (DEH-PPV) and oligomers of polyoctahedral silsequioxanes (POSS).

The scheme in the top two lines results in an A-B linking scheme. When too many chains attach to the microbead, a bridge may form between two adjacent chains because they all use the same linkers. When 2 neighboring chains terminate with an A as shown in the diagrams, when the process adds the B-shape-B, the first chain receives it first. This chain can then react with the second chain, which forms a bridge, rather than keeping the polymer chains separate.

One solution to avoid chains is to use different linkers. As shown in the bottom two rows of FIG. 2 show, the linker is A-C instead of A-A, and the rigid monomers are B-shape-D. The materials may be selected such that the links are AB and CD, but not AD or BC. This will prevent the bridging problem, but the chemistry is more complicated to implement. Possible linker pairs (for either AB or CD) include azide-alkyne "click" reactions, hydroxyl-carboxylic acid, amine-carboxylic acid, amine-anhydride, Michael addition, Diels-Alder, thiol-ene, and thiol-thiol reactions. In another embodiment, the linkers could already be pre-attached to the rigid information-encoding units. Such a case will still make use of one or more pairs of functional groups to impose the sequential addition of only one repeat unit per chain.

Figure 3:
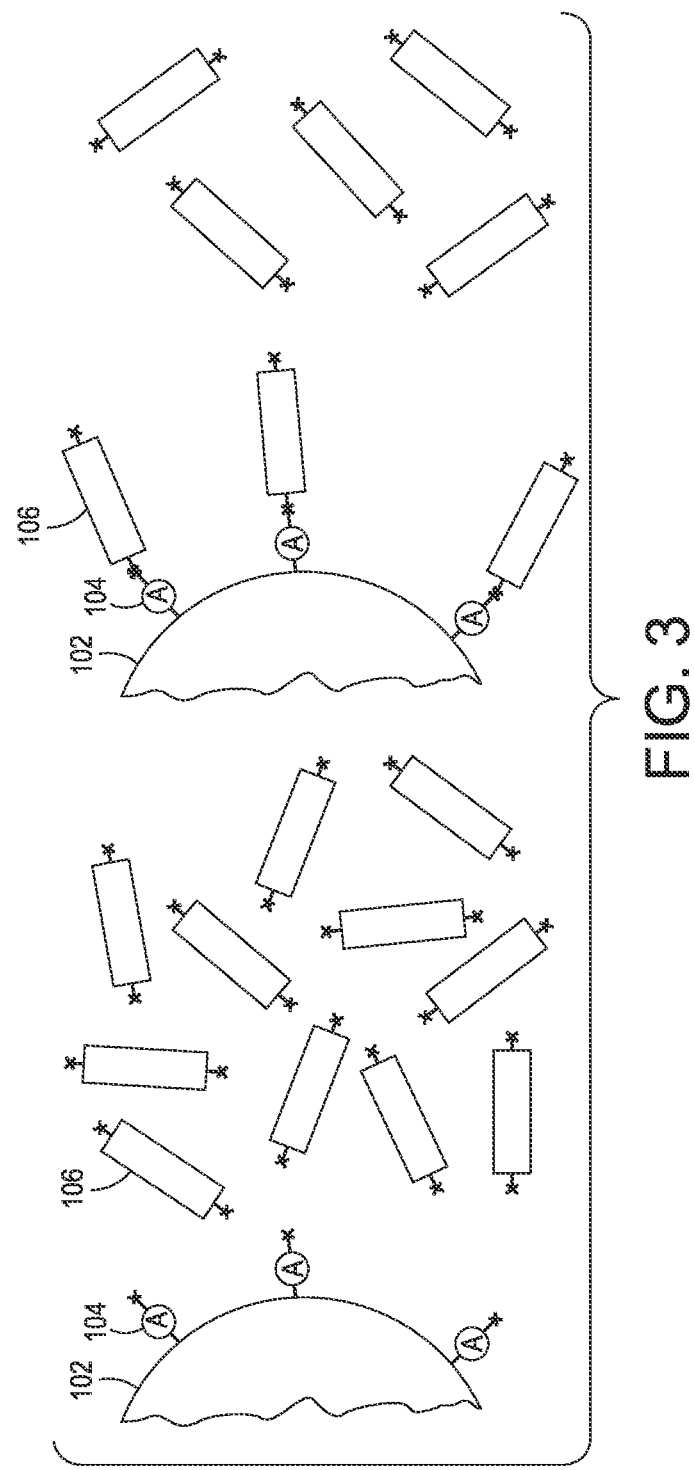
FIGS. 3-5 show embodiments of encoding data using monomer sequencing.
Figure 4:
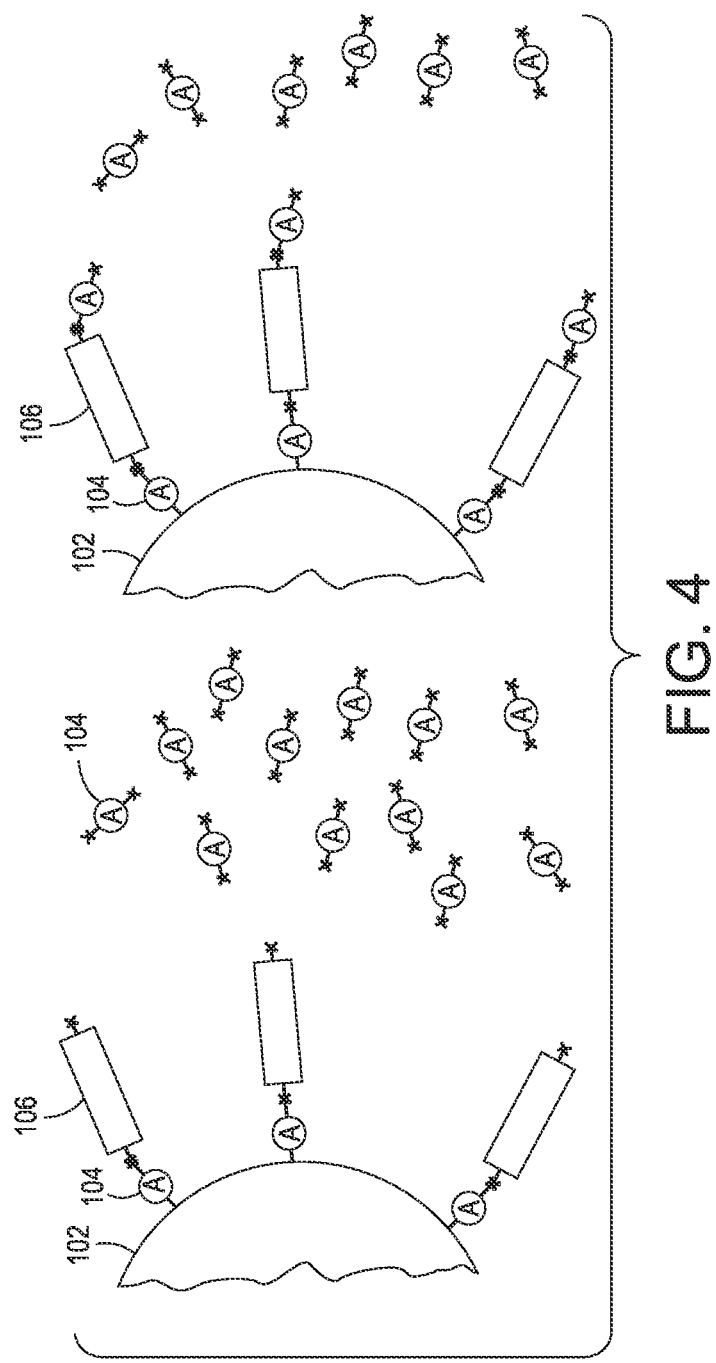
Figure 5:
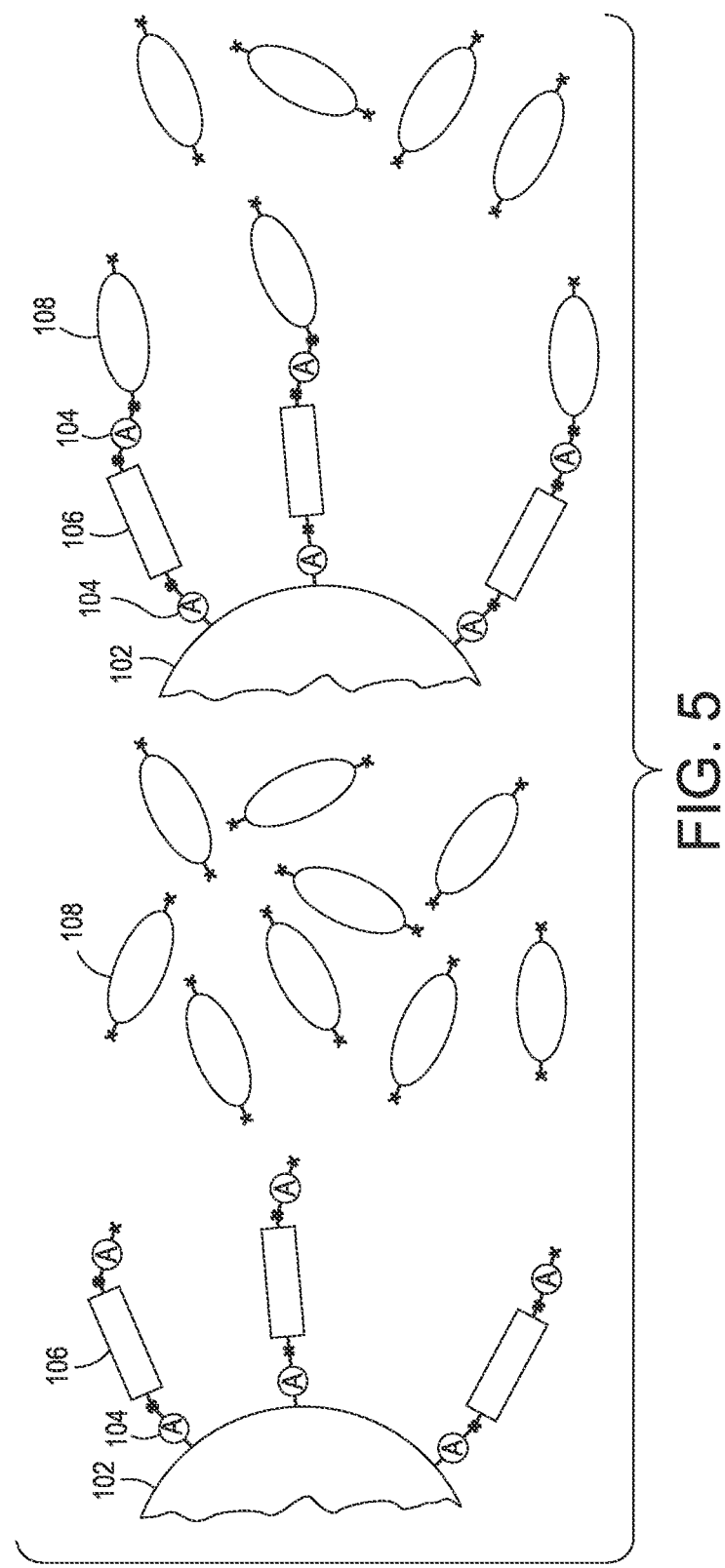

As shown in FIGS. 3-5, the polymer chains are formed by linking monomers together in a particular sequence. The polymer chains are 'anchored' by a microbead 102. Initially, a linking compound 104 such as an oligomer is deposited into the microwells to attach to the surface of the microbead. Then a solution containing the first monomer 106 is deposited into the microwells with reagents or other polymerization agents to cause the monomer 106 to attach to the linking particle as shown in the left side of FIG. 3. The monomer 106 is one 'character' in the polymer sequence. The first monomer 106 is deposited on the microwells in excess to promote uniform grafting of the monomer across all propagating chains in the microbead 102. All unreacted monomers are then flushed away in a manner to be described later.

In another embodiment, a single character can be composed of a short sequence of monomers (i.e. a codon), or the adjacency of monomers. E.g., in a character construct composed of 4 monomers locations and two types of monomers, X, and Y, there are 16 possible characters. The characters in an encoding system can be all the same length, or different lengths. In a character composed of the adjacency of monomers, the transition from one type of monomer or codon to another is what encodes the character information.

In FIG. 4, on the left side, one can see that the linker 104 is then deposited into the microwells to attach to the previously attached monomer 106. The attachment is shown in FIG. 4 on the right side. As will be discussed in more detail on the sequencing or 'readout' process, the linkers both allow formation of the polymer, and allows for spacing between characters in the data string stored as the polymer chain.

In FIG. 5, a new monomer 108 is deposited into the microwell and then processed to cause them to attach to the linking particles 104. The determination of which monomers and linkers are used depends upon the nature of the materials used and how it is deposited.

Figure 6:
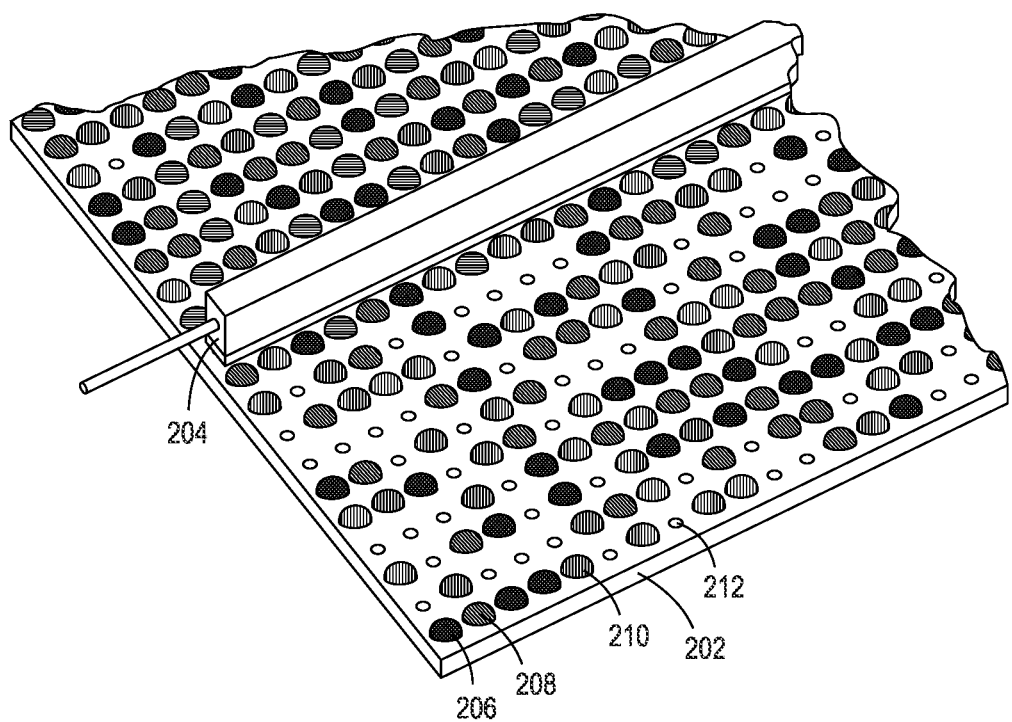
FIG. 6 shows an embodiment of a dispensing system to synthesize sequence-controlled polymers.

One manner in which these materials could be deposited and the polymers synthesized may involve an inkjet printer. Each microwell into which the materials are deposited may have a porous membrane as support structure and may have a vacuum chuck underneath it to facilitate the drainage of excess solution. The use of an inkjet printer allows for massively parallel formation of the polymer chains with different sequences, and therefore faster storage of data. FIG. 6 shows one example of a print head 204 depositing materials into an array 202 of microwells such as 212.

In one embodiment there would be six print heads, for a 4-character (monomer) alphabet. A first print head would deposit the linking material into each microwell that contains a microbead, such those made of silica. A second print head then deposits a 'character' polymer in the selected wells that have that as their first monomer in the sequence. A third, cleaning, print head, would then wash the microwells by depositing a flushing liquid to remove the excess character monomer and the vacuum chuck ensures drainage of both the excess monomer and linker. Depending upon the materials used, the cleaning step may be necessary after the linker or only after linker and character monomer pairs. The first print head then deposits the linker into all the microwells, then a fourth print head deposits the second character monomer in to those wells that have it as their second character. In another embodiment, the four different print heads depositing the character monomers pass the substrate consecutively after the first print head (linker). Each microwell receives only one of the four different characters in this print step but all the characters corresponding to that spot in the monomer sequence are printed simultaneously.

In another embodiment, the encoding monomers already have the linker bonded to their structure.

This process continues until each microwell has multiple copies of a particular sequence. Note that each print head will make trips at each character deposition. For some sequences, the 'first' monomer may actually occur third in their sequence, so the first print head may have to make trips to deposit its monomer when it happens first, second, third and fourth. The deposition of the monomers may also include the reagents or other polymerizing materials that cause the monomers and linkers to form polymer chains. The microwells or print head itself may allow the reaction solution to be heated or exposed to electromagnetic radiation, or exposed to another energy source to enable polymerization.

One should note that the use of a print head provides one example of a polymer synthesize in which polymer chains can be formed. Other forms of synthesis are of course possible, including flow chemistry, microfluidic reactors, reactions that rely on protection and deprotection steps, as used in de novo DNA synthesis, and microwells/surface based catalysis, etc.

In addition to inkjet printing allowing massive parallelization of polymers for storage applications, inkjet printing and the alternating linker-monomer-linker scheme in an on-demand sequence can be used for highly parallelized synthesis of polymers in general. These applications may include self-assembling biomolecules, polymer-drug design, or combinatorial materials development.

Figure 7:
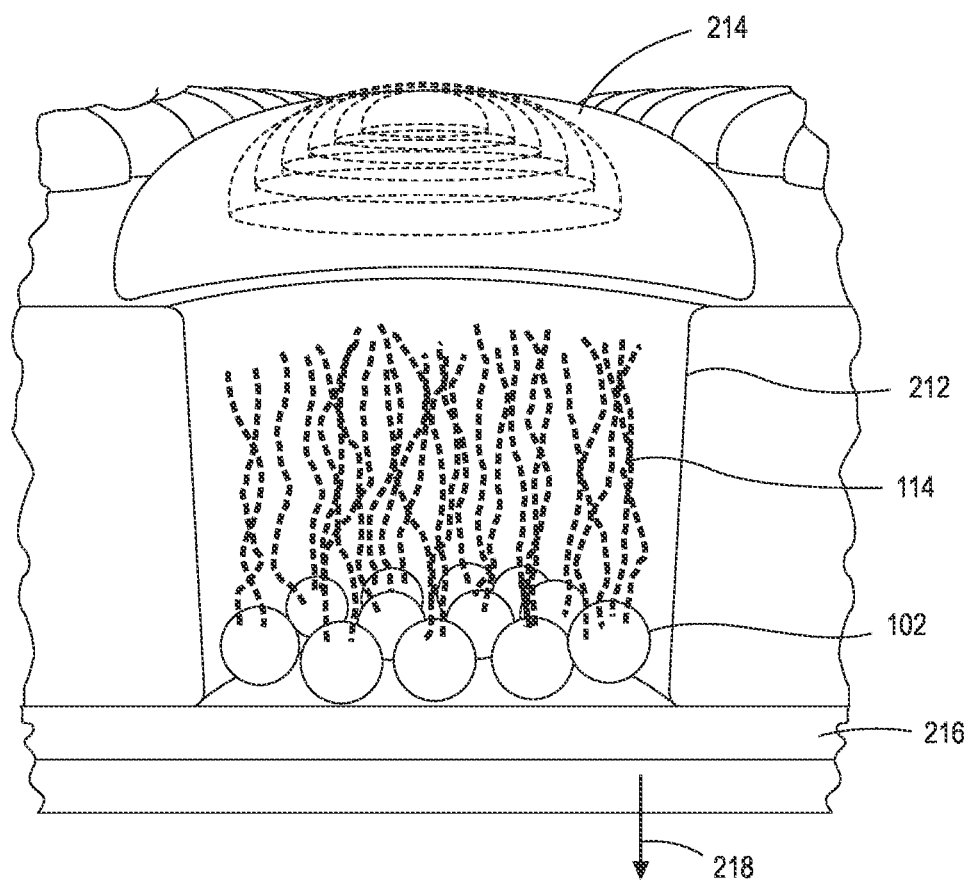
FIG. 7 shows an embodiment of a microwell containing sequence-controlled polymers attached to microbeads.

FIG. 7 shows an embodiment of a microwell 212 having multiple microbeads 102, each with multiple copies of the same monomer sequence, such as 114, attached. The dimensions of the microwell 212 are such that an individual droplet of fluid 214 dispensed by the print head 204 completely covers and fills up the volume of the microwell. Droplets dispensed by inkjet printers range in size from 15-200 microns and the size range of about 50-200 microns are of interest here. The microwells 212 will then have diameters of about 20-150 microns with depths of similar dimensions. The porous membrane support 216 is micro- or nanoporous and its effective porosity dictates the rate of fluid drainage in the microwell. This drainage rate is also affected by the backpressure imposed by a vacuum 218 chuck, in common to all microwells. In some embodiments, the membrane support is of a ceramic material such as anodic aluminum oxide or nanoporous silica. The pores of the membrane should be small enough such that the microbeads 102 which have dimensions of about 1-20 microns can be supported. In some embodiments, the microbeads could be made of metal or ceramic materials such as iron, iron oxide or silica. The rate of drainage in the microwell is to be tuned such that the fluid resides in the microwell long enough for the reactions illustrated in FIGS. 3-5 to occur. The reactant concentration in the fluid droplets will be tuned to promote fast reaction times and high grafting efficiency.

The microbeads and their chains in each microwell are then encapsulated by an encapsulation system with a microfluidic droplet that includes the ability to 'address' the microfluidic droplet. In one embodiment, an address-encoding fluorescent dye combination is added to the droplets. One method of selectively dispensing these fluorescent dye combinations is with the use of an inkjet printer. Different dyes, for example about 4-6 fluorescent dyes with different peak emission wavelengths across the optical spectrum, and different intensities of the emission of dyes, about 10-14 per dye, allow for a large number of optical addresses. The different intensities of the emission of the dyes can be achieved by varying the concentration of the dye dispensed into the fluid volume.

In some embodiments, the polymer chains 114 can also be chemically-cleaved from the microbeads 102 prior to encapsulation and introduction of the optical address. The cleavage reaction can be triggered by heat, light, some other specific energy source or a chemical stimulus such that the chain cleavage only occurs on-demand. In some embodiments, the microbeads 102 can also be destroyed prior to encapsulation of the polymer chains 114 in the droplet, e.g. using chemical etching agents that are reactive towards the microbead but not the polymer chains. In these embodiments, the microbeads can be made of ceramics or metals that are easy to dissolve or etch. Other possible addressing schemes include unique solutes being added to the droplets, such as salts, functionalized nanoparticle labels, etc. These other addressing schemes may allow addressing means using non-optical probes, e.g. electrochemical, electrostatic, magnetophoretic, etc.

Figure 8:
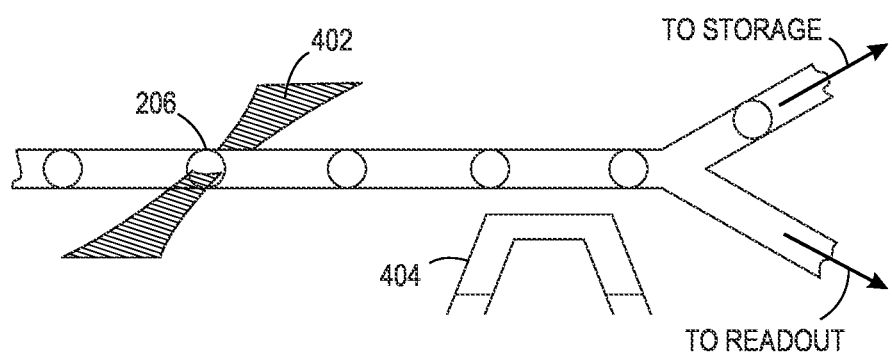
FIG. 8 shows an embodiment of a sorting system to sort microfluidic droplets.

As discussed above, once the droplets are addressed they may be stored. When access to the data they contain in desired, they are brought out of storage and sorted. In FIG. 8, one possible sorting system is shown. The droplets may undergo the sorting process whether the system is applying a 'search and sort' operation to look for particular segments of the data, similar to random access memory operations, or a bulk readout of the entire storage or a portion of it. In the case of bulk readout, the entire archive is to be read but the use of the optical address detection scheme in FIG. 8 is still necessary to identify the address encoded in each droplet.

In FIG. 8, the embodiments of the droplets such as 206 have fluorescent dyes in them. An initial sort is performed to identify the color and intensity information of the droplet associated with a particular polymer chain using a light source that causes the dye to fluoresce with a specific combination of intensities for each color. For the case of bulk readout where the entire data archive stored is to be readout, this process allows association of the particular droplet to the particular nanopore it will be directed to. For the case of the "search and sort" operation where the system attempts to find specific segments of the data, the obtained optical address is then compared to an address list of desired segments or files. The optical address is then used to trigger an actuator, which may include electric field-based actuators, magnetic field-based actuators, acoustic tweezers, optical tweezers or switchable microwaves. The action of the actuator will then direct the droplet either to the readout module, which could be a specific nanopore in an array, or back to storage.

As the droplets undergo sorting, they are deposited into a holding structure that has a capability of performing sequencing. One embodiment, discussed here, uses a solid-state nanopore array. Other options include biological nanopore structures, mass spectrometers either in conventional or microfluidic form, Fourier Transform infrared (FTIR) spectroscopy, nuclear magnetic resonance (NMR) spectroscopy, etc.

Figure 9:
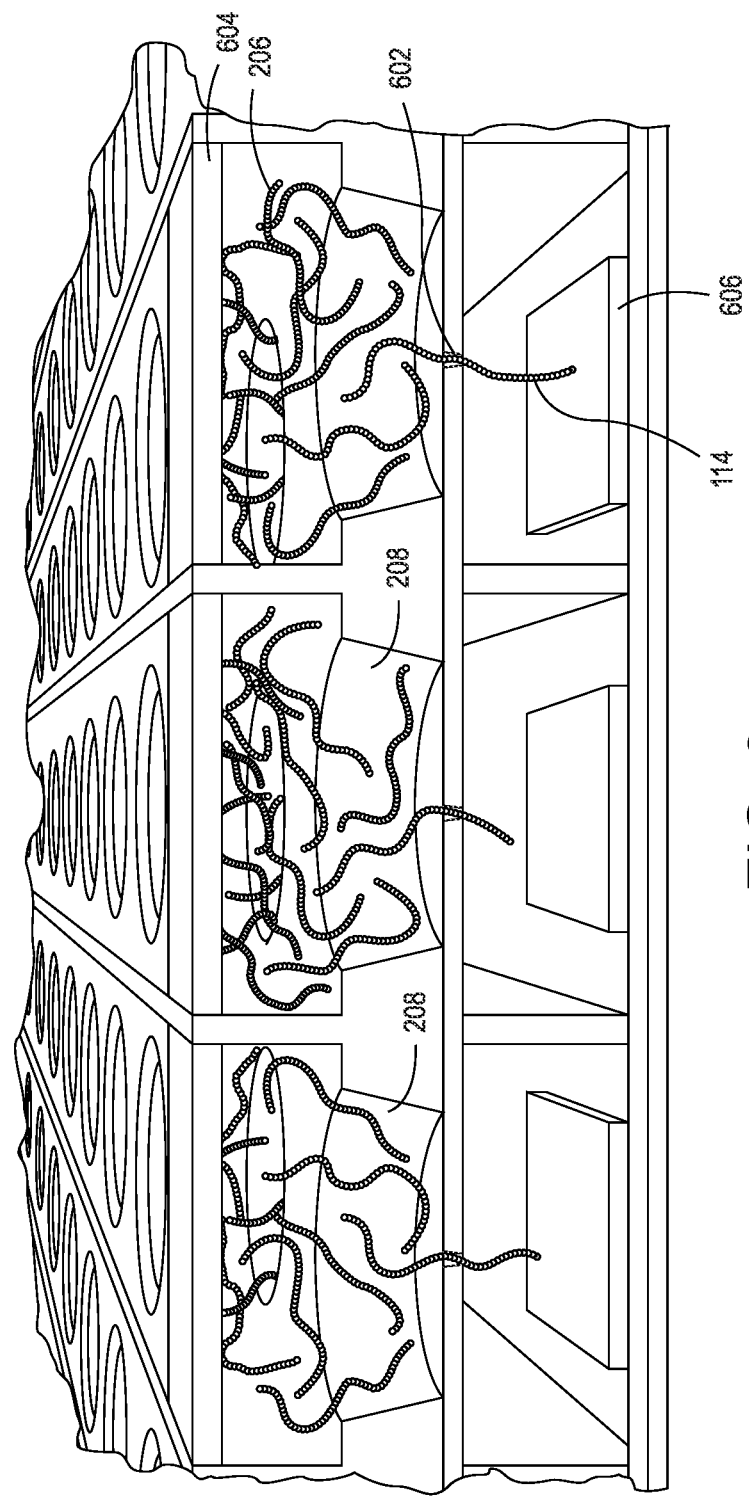
FIG. 9 shows an embodiment of sequence-controlled polymers in a nanopore array.

In the embodiment show in FIG. 9, a nanopore structure has a support structure that contains the microfluidic droplets such as 206, 208 and 210. The nanopore structure has a common electrode 604 that may be indium tin oxide (ITO) or some form of conducting glass, and individual pore electrodes 600. The pore structures such as 602 allow polymer chains to pass through them while having a current applied that can then sequence the polymer chain to determine which monomer sequence it has. This is shown in more detail in FIG. 10. The pore electrodes 600 in different nanopores are electrically isolated so as to allow independent readout of polymer chains from multiple droplets simultaneously.

Figure 10:
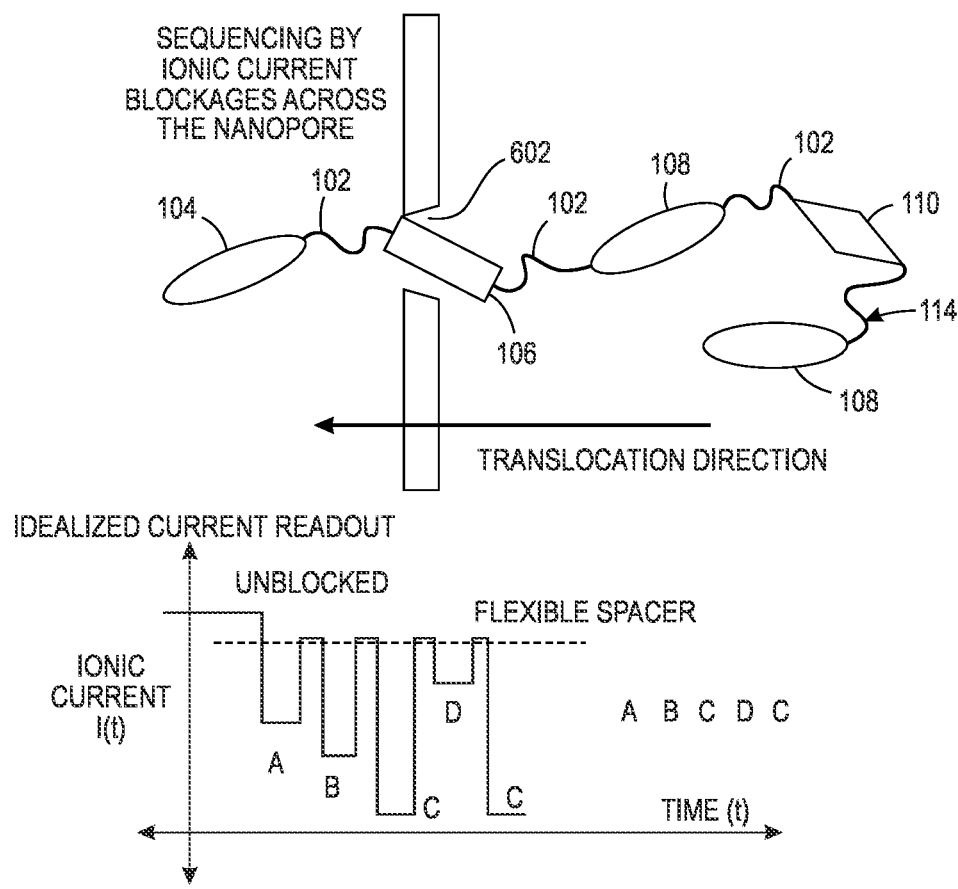
FIG. 10 shows a representation of the readout process for obtaining the monomer sequence from the sequence-controlled polymer

In FIG. 10, a polymer chain 114 passes through the nanopore structure and has an associated ionic current readout to it. As mentioned above, the polymers or specific segments of the polymers, such as the flexible linkers, are charged. In this example, the polymer chain 114 has monomers 104, 106, 108 and 110, as well as linker 102. The polymer chain 114 is solvated in a buffer which contains ions. When a voltage is applied across the nanopore, ionic current is generated across it due to motion of ions through the nanopore. As the polymer chain blocks the pore, the ionic current across the pore drops due to geometric exclusion. The readout, shown below, then detects each monomer based on the blocked ionic current associated to it shown in the ionic current profile. The resulting profile is then compared to a table or other reference and it is determined that it corresponds to the sequence A-B-C-D-C.

During this readout phase, as well as at other points, error correction can occur. There are multiple copies of the polymer chain in the droplet. Multiple copies could be accessed and sequenced and then the data from each can be compared to determine the correct sequence. Some chains may be missing monomers, have duplicate characters, or may have undergone bridging, mentioned above. By comparing multiple copies, the system can determine the correct sequence to be derived from that polymer chain. Once the sequence has been determined, it can be converted back to the digital data that was originally stored. The converter may comprise a computer or other instrument that can convert monomer sequence into digital data. After readout, the microfluidic droplets that contain the rest of the polymer chains will then be returned to storage.

An advantage of the SCRIPT polymer-based system involves the amount of data stored in the sequences. In DNA data storage systems, each DNA strand typically has a length of 150-200 nucleotides. A large number of these nucleotides per strand are allocated to primer and spacer sequences as well as a unique address. This unique address is typically used for random-access capability in the DNA archive but requires that multiple unique addresses be generated depending on the level of random access. This imposes a constraint on the amount of information payload that can be carried by each individual strand. One of the many advantages of the SCRIPT system is that the addressing of the microfluidic droplets is external to the polymer chains, so no space need be reserved in the polymer chains for the address. As such, much of the chain length goes to the information payload. Another advantage of the SCRIPT system is that chains can be as large as $10^3$-$10^4$ information containing units/oligomers. This means that one needs to handle a smaller number of polymer chains compared to a strands in a DNA-based scheme to store the same amount of data.

In a particular embodiment of the device, data will be stored in the form of micron-sized microfluidic droplets that may be roughly 25 microns in diameter although in some embodiments, the droplets could range in size from 10-50 microns. For the case of 25 micron droplets, one terabyte ($10^{12}$ bytes) of data can be stored in a total fluid volume of about 0.71 milliliters (mL), while 1 Exabyte ($10^{18}$ bytes) of data can be stored in a total fluid volume of about 1 meter cubed, roughly the size of a large deep freezer. In contrast, Exabyte-sized state-of-the-art data archives stored in magnetic tape is stored in a spatial footprint of about 750,000 square feet. In another embodiment, the polymer contents of the fluidic droplets can be dehydrated to further reduce the spatial footprint. The maximum gravimetric density the system can approach in this manner is about 315 Exabytes per gram, close to the theoretical maximum gravimetric information density calculated for state-of-the-art DNA data storage.

The SCRIPT system offers several advantages over both commercial, and DNA and polymer options. Compared to conventional commercial data storage technologies, such as magnetic tape, HDD, and SDD, the embodiments offer several advantages. The information storage medium has a high volumetric and gravimetric information density which allows more data to be stored at a smaller spatial footprint. The smaller spatial footprint, in turn requires a smaller energy budget and will be cheaper to operate. The information storage medium has a low passive degradation rate so the media can outlast most conventional methods, including magnetic tape which can only last for decades.

Compared to current demonstrations of DNA and polymer data storage, the embodiments offer several advantages. SCRIPT targets the non-biological synthetic polymer space which offers 1) a larger potential monomer alphabet for encoding data beyond the four-letter alphabet of DNA nucleotides, 2) the potential for synthesizing polymer chains much longer than DNA oligonucleotides, and 3) the potential for designing the polymer in view of a target sequencing method that is already scalable. SCRIPT enables random access using specific combinations of optical fluorescent dyes that are dissolved in the solvent in the microfluidic droplet and, hence, are external to the polymer chains. In contrast, random access schemes in DNA data storage typically use specially-designed primer sequences which consume part of the total nucleotides of the oligomers. SCRIPT uses an inkjet-based synthesis approach that is scalable by design and can allow synthesis of 1 TB of data in 1 day. The largest reported DNA-stored data is 200 MB.

In addition, SCRIPT uses solid-state nanopore sequencing for information retrieval in which the arrays can be designed to enable less ambiguous sequence determination from our polymer architecture. The polymer architecture of the embodiments, both the size of the rigid monomers and the length of the flexible spacers, can be tuned specifically to enable easy solid-state nanopore sequencing. SCRIPT is based on physical hardware that has a small spatial footprint and that can enable a self-contained workflow for both information writing and reading. Most DNA data storage systems still rely on external facilities for the de novo DNA synthesis.

It should also be appreciated that the method and systems for synthesizing alternating rod-coil copolymers (i.e. flexible linkers and rigid, rod-like units) described in FIGS. 2-7 can be used for polymer synthesis in general. The use of the inkjet-based system will allow massively parallel digital synthesis of polymers with controlled sequences of the architecture described in FIGS. 3-5 using the described monomer sets and linking chemistries in FIG. 2 in a manner that is scalable. We describe this system here as a module for synthesizing the polymers as means of storing data but the system could find applications in other areas such as in combinatorial materials design and screening and in the synthesis and discovery of new polymer-based drugs or drug delivery vehicles.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of storing digital data in non-biological sequence-controlled polymers, comprising:
   converting a digital data file into a monomer block sequence;

synthesizing polymer chains according to the monomer block sequence, the polymer chains being non-biological sequence-controlled polymers, the polymer chains comprising alternating segments of rigid monomer blocks and flexible linkers having a persistence length of no more than two nanometers;

encapsulating the polymer chains into microfluidic droplets;

providing the microfluidic droplets with addresses by dyeing the microfluidic droplets with one or more optical fluorescent dyes; and storing the microfluidic droplets organized by the addresses in a storage.

2. The method as claimed in claim 1, further comprising:
sorting the microfluidic droplets according to the addresses;
sequencing the polymer chains to derive the monomer block sequence; and
converting the monomer block sequence to digital data.

3. The method as claimed in claim 1, wherein converting the digital file into a monomer block sequence uses a monomer alphabet having at least 2 characters.

4. The method as claimed in claim 1, wherein synthesizing polymer chains comprises using a first linker to attach a first monomer to a microbead, then repetitively attaching second linkers and then monomers to form the polymer chains, wherein the first linker is one of either the same as the second linkers or different than the second linkers.

5. The method as claimed in claim 4, wherein the first and second linkers are flexible segments of polymers that are charged.

6. The method as claimed in claim 1, wherein monomers that are used to encode the digital data are rigid and bulky molecular segments of distinct sizes.

7. The method as claimed in claim 1, wherein synthesizing the polymer chains comprises inkjet printing the reactants, reaction-promoting additives, the first and second linkers and the rigid monomer blocks into an array of microwells.

8. The method as claimed in claim 1, wherein synthesizing the polymer chains comprises one of flow chemistry, microfluidic reactors, microwell/surface-based catalysis, exposing a reaction solution to one of heat or electromagnetic radiation.

9. The method as claimed in claim 2, wherein sorting the microfluidic droplets comprises at least one of using electric fields, magnetic fields, light sources, using microvalves, and acoustic tweezers.

10. The method as claimed in claim 2, wherein sorting the microfluidic droplets comprises applying a light to the microfluidic droplets to cause the one or more optical fluorescent dyes to fluoresce and detecting the fluorescence as a fluorescence signature.

11. The method as claimed in claim 2, wherein sequencing the polymer chains comprises at least one of: using solid-state nanopores, biological nanopores, using mass spectrometry, FTIR spectroscopy, NMR spectroscopy, AFM and probe-based microscopy.

12. The method as claimed in claim 2, wherein sequencing the polymer chains comprises applying a voltage across a nanopore which induces the polymer chains to pass through a nanopore and then recording resulting current measurements.

13. The method as claimed in claim 12, wherein converting the monomer block sequence to digital data comprises correlating the resulting current measurements with particular monomers and then converting the monomer block sequence to binary data.

14. A polymer data storage system, comprising:
a first converter to convert digital data to a monomer sequence
a polymer synthesizer to produce polymer chains according to the monomer sequence using linkers having a persistence length of no more than two nanometers between monomers, the polymer chains being non-biological sequence-controlled polymers;
a fluidic encapsulation system to encapsulate the polymer chains in microfluidic droplets and to apply addressing materials to the microfluidic droplets;
a storage for storing the microfluidic droplets;
a droplet sorting system having at least an actuator to sort the microfluidic droplets;
a sequencer to derive the monomer sequence from the polymer chains contained in the microfluidic droplets; and
a second converter to convert the monomer sequence to digital data.

15. The system as claimed in claim 14, wherein the polymer synthesizer comprises at Last one of an inkjet printer, a flow reactor, a microfluidic reactor, or a microwell/surface-based catalysis fixture.

16. The system as claimed in claim 14, wherein the storage comprises one of a liquid storage, a frozen storage, a polymer shell encapsulated storage or a dehydrated storage.

17. The system as claimed in claim 14, wherein the actuator comprises at least one of a light source, an electric actuator, a magnetic actuator, microvalves, and acoustic tweezers.

18. The system as claimed in claim 14, wherein the sequencer comprises one of a solid-state nanopore array, a biological nanopore array, a mass spectrometer, a Fourier Transform infrared spectrometer, AFM, probe-based microscopy, electron microscopy, or a nuclear magnetic resonance spectrometer.

19. A composition of matter comprising polymer chains, the polymer chains being non-biological sequence-controlled polymer, the polymer chains comprising alternating segments of flexible small persistence length linkers having a persistence length of no more than two nanometers and one or more rigid monomer blocks, wherein the one or more rigid monomer blocks are in a sequence in the polymer chains that represents digital data.

* * * * *